United States Patent [19]
Russell

[11] Patent Number: 5,830,893
[45] Date of Patent: Nov. 3, 1998

[54] TREATMENT OF EQUINE PROTOZOAN MYELOENCEPHALITIS USING TRIAZINEDIONES

[75] Inventor: Meri Charmyne Russell, Des Moines, Iowa

[73] Assignee: Mortar & Pestle Veterinary Pharmacy, Inc., Des Moines, Id.

[21] Appl. No.: 844,855

[22] Filed: Apr. 23, 1997

[51] Int. Cl.$^6$ .................. A61K 31/53; A61K 31/495; A61K 31/19
[52] U.S. Cl. ................... 514/242; 514/252; 514/557
[58] Field of Search ..................... 514/242, 252, 514/557

[56] References Cited

U.S. PATENT DOCUMENTS

| | | | |
|---|---|---|---|
| 4,631,278 | 12/1986 | Boeckx et al. | 514/242 |
| 4,912,106 | 3/1990 | Boeckx et al. | 514/236.2 |
| 4,935,423 | 6/1990 | Lindner et al. | 514/242 |
| 5,114,938 | 5/1992 | Lindner et al. | 514/242 |
| 5,141,938 | 8/1992 | Lindner et al. | 514/242 |
| 5,188,832 | 2/1993 | Mehlhorn et al. | 424/405 |
| 5,256,631 | 10/1993 | Lindner et al. | 424/405 |
| 5,464,837 | 11/1995 | Mehlhorn et al. | 363/124 |

FOREIGN PATENT DOCUMENTS

| | | |
|---|---|---|
| 0170 316 A2 | 2/1986 | European Pat. Off. . |
| 0170 316 B2 | 2/1986 | European Pat. Off. . |

OTHER PUBLICATIONS

"Diclazuril", The Merck Index, Item No. 3130.

Vanparijs et al., "Diclazuril, a New Broad–Spectrum Anticoccidial for Chickens 3. Floor–Pen Trials", Poultry Science, (1990) vol. 69, pp. 60–64.

Vanparijs et al., "Efficacy of Diclazuril against Turkey Coccidiosis in a Floor–Pen Experiment", Avian Diseases (1989), vol. 33, pp. 479–481.

Maes et al., "In Vivo Action of the Anticoccidial Diclazuril (Clinacox) on the Developmental Stages of *Eimeria Tenella*: A Histological Study", J. Prasitol, vol. 74, No. 6, (1988), pp. 931–938.

Verheyen et al., "In Vivo Action of the Anticoccidial Diclazuril (Clinacox) on the Developmental Stages of *Eimeria Tenella*: An Ultrastructural Evaluation", J. Parasitol, vol. 74, No. 6, (1988) pp. 939–949.

"Equine Protozoal Myelitis Workshop: Summary for the Horseman", Grayson Jockey Club Research Foundation EPM Seminar, Mar. 8, 1996.

Jill Beech, "Equine Protozoan Encephalomyelitis", Veterinary Medicine/Small Animal Clinician, Dec. 1974, pp. 1562–1566.

Granstrom et al., "EPM Seminar", The Horse, Nov. 1995, pp. 14–23.

Welsch et al., "Update on Equine Therapeutics: Treatment of Equine Protozoal Myeloencephalitis", Equine: The Compendium North American Edition, pp. 1599–1602.

Kayembe et al., "Diclazuril for Isospora Belli Infection in AIDS", The Lancet, Jun. 17, 1989, vol. 1, pp. 1397–1398.

Hamir et al., "Immunohistochemical Study to Demonstrate Sarcocystis Neurona in Equine Protozoal Myeloencephalitis", J. Vet. Diagn. Invest. Jul. 1993, vol. 5, No. 3 pp. 418–422.

Bowman et al., "Characterization of Sarcocystis Neurona from a Thoroughbred with Equine Protozoal Myeloencehalitis", Cornell Vet. Jan. 1992, vol. 82, No. 1, pp. 41–52.

Boy et al., "Protozoal Encephalomyelitis in Horses: 82 Cases (1972–1986)", J. Am. Vet. Med. Assoc., Feb. 15, 1990, vol. 196, No. 4, pp. 632–634.

Madigan et al., "Equine Protozoal Myeloencephalitis", Vet. Clin. North Am. Equine Pract., Aug. 1987, vol. 3, No. 2, pp. 397–403.

Beech , J., "Equine Degenerative Myeloencephalopathy", Vet. Clin. North Am. Equine Pract., Aug. 1987, vol. 3, No. 2, pp. 379–383.

*Primary Examiner*—Kevin E. Weddington
*Attorney, Agent, or Firm*—Giberto M. Villacorta, Pepper Hamilton LLP

[57] ABSTRACT

The present invention relates to compositions and methods for treating equines, such as horses, afflicted with equine protozoan myeloencephalitis or EPM. The therapeutic composition comprises one or more triazinediones.

27 Claims, No Drawings

TREATMENT OF EQUINE PROTOZOAN MYELOENCEPHALITIS USING TRIAZINEDIONES

FIELD OF THE INVENTION

The present invention relates to compositions and methods for treating equines, such as horses, afflicted with equine protozoan myeloencephalitis or EPM. EPM is a debilitating neurologic disease of equines, which can affect the brain, the brain stem, spinal cord, or any combination of these three areas of the equine's central nervous system. EPM is caused by infection by the protozoan parasite *Sarcocystis neurona* (recently referred to as *Sarcocystis falcatula*). There is no vaccine or approved animal drug product available for effectively treating this disease in horses.

BACKGROUND OF THE INVENTION

Although the symptoms and effects of EPM have been recognized since the 1970's, it was not until 1991 that the protozoan parasite that causes EPM was cultured from a horse and given the name *Sarcocystis neurona*. The horse is an aberrant, dead-end host, as infectious forms of the parasite are not passed from horse to horse or from infected horse to a definitive or true intermediate host. Recent investigations indicate that the feces of opossum (the definitive host) may be the source of the infection for horses.

EPM occurs in much of North America. Surveys, which were conducted in central Kentucky, one county in Pennsylvania and the entire states of Ohio and Oregon, have revealed that approximately fifty percent (50%) of the horses in the surveyed areas have been exposed to the above-noted protozoan parasite. A positive serum test indicates exposure to the parasite, not necessarily the presence of an active form of the disease. The incidence of the active disease is much lower.

In studies that looked at the distribution of seropositive cases geographically, it was found that climatic factors might affect exposure rates; i.e., an increase of freezing days or a very hot environment was associated with a decrease in the numbers of horses exposed to the parasite. EPM appears to have a sporadic distribution, although outbreaks have been reported on farms in Kentucky, Ohio, Indiana, Michigan and Florida.

A horse of any age, breed, or sex may be affected by EPM. The disease has been reported in a horse of two months of age, as well as one in its thirties. In fact, any horse demonstrating neurologic abnormalities may be infected.

Clinical signs of a condition depend on the location of the organism within the central nervous system. These signs include weakness, malposition of a limb, muscle atrophy, spinal ataxia, or "wobbling" and/or head tilt with asymmetry of the face (e.g., eyelid, ear, or lip). A severely EPM-affected horse may go down and be unable to rise. Lameness not traceable to orthopedic disease or any combination of the above signs may occur in early or less severe infections. Other unusual signs may also occur.

In most cases, an affected horse is bright and alert with a normal appetite, although it may be dysphagic (i.e., unable to eat) and may act as if it is choked with feed material coming from its nose. Hematological and biochemical blood values are usually in the normal range.

Diagnosis of EPM is based on clinical signs and on testing of the horse's cerebrospinal fluid (CSF). Originally, the diagnosis was based on the presence of antibodies to *Sarcocystis neurona* in serum, though it is now known that a positive serum test cannot be used to make a diagnosis; such positive serum test simply indicates exposure to the parasite, not necessarily presence of the disease. Cerebral spinal fluid testing is now believed to be the most useful test to assist in the diagnosis of this disease in a live horse.

Currently available treatment of horses with EPM is expensive and typically requires a treatment period of at least ninety (90) days. In some cases, treatment lasts indefinitely. This current treatment involves the adaptation of tablets intended for human use. Thus, pyrimethamine tablets are administered along with tablets containing a trimethoprim-sulfonamide combination. These tablets contain pyrimethamine and are administered along with tablets containing a trimethoprim-sulfonamide. These medications should be administered one hour prior to feeding hay and are accompanied with frequent, periodic, veterinary, neurologic examinations during the treatment period.

Discontinuation of therapy is usually based on the administration of medication thirty days beyond the plateau of clinical improvement or disappearance of antibody to the protozoa from the CSF. Suboptimal dosing or intermittent therapy has no proven efficacy.

Adverse effects of therapy may include anemia, abortion, diarrhea and low white blood cell counts. Both medications for treatment of EPM inhibit folic acid metabolism. Unlike horses, however, the protozoan is unable to utilize preformed folic acid. Supplementation with folic acid (40 mg orally, once a day) and/or brewer's yeast may help prevent adverse side effects. It is suggested, however, that folic acid not be administered at the same time as the pyrimethamine because of competitive inhibition and absorption.

On the other hand, a number of literature articles describe the treatment of *Eimeria* or *Isospora belli* with diclazuril. Vanparijs et al. *Poultry Sci.* (1990) 69:60–64, disclose the use of diclazuril to treat chickens infected with six Eimeria species. In a separate reference, Vanparijs et al. *Avian Diseases* (1989) 33:479–481, disclose the efficacy of diclazuril against three Eimeria species in turkeys. Lastly, Kayembe et al., disclose the use of diclazuril to treat *Isospora belli* infection in AIDS patients (See e.g. Kayembe et al. *Lancet* (1989) 1:1397–1398). These references, however, do not suggest or teach a method for treating subjects infected with an organism of the genus Sarcocystidae let alone treating equines suffering from EPM.

The patent literature also includes many descriptions of methods for treating coccidiosis in chickens and fish parasites. For instance, in U.S. Pat. Nos. 5,464,837 and 5,188,832, Mehlhorn et al. disclose methods for controlling fish parashtes by administering to fish having such parasites an effective amount of at least one substituted 1,2,4-triazinedione. Linder et al., in U.S. Pat. Nos. 5,256,631; 5,141,938; 5,114,938; 4,935,423 disclose general methods of treatment of coccidiosis in poultry, in particular chickens, and parasites in fish by administering substituted triazinediones. Diclazuril, 2,6-dichloro-α-(4-chlorophenyl)-4-(4,5-dihydro-3,5-dioxo-1,2,4-triazin-2(3H)-yl) benzeneacetonitrile, is a known compound and is listed in The Merck Index as a coccidiostat.

In U.S. Pat. Nos. 4,912,106 and 4,631,278, and in European Patent No. 170 316, Boeckx et al. disclose substituted triazinedione to treat chickens suffering from *Eimeria tenella*. However, Boeckx et al. do not disclose methods of treating sarcocystidae by administering triazinediones, much less by using diclazuril.

Hence, despite a great deal of past and on-going effort, there remains an unfulfilled need for a treatment for EPM-afflicted equines, particularly horses, which is not only effective but is also convenient to administer to maximize compliance and reduce the emergence of resistant strains. In particular, prior compositions for the treatment of EPM involve three-component mixtures, including pyrimethamine, sulfadiazine and trimethoprim. Moreover, where prior compositions contained pyrimethamine and sulfadiazine as the active ingredients, such compositions used very small ratios of pyrimethamine to sulfadiazine limiting their effectiveness to treating malaria only and hampering their usefulness in other pathological conditions, like protozoan-mediated diseases, especially EPM. As for triazinediones, the description in the art for the treatment of coccidiosis fails to teach, disclose, or suggest the use of triazinediones for the treatment of EPM. The fact is, there is currently no approved drug or drug combination for the treatment of EPM.

SUMMARY OF THE INVENTION

Quite surprisingly, it has now been discovered that an effective, convenient method of treating EPM is realized by the administration to an equine suspected of being afflicted with EPM of Therapeutically effective amounts of triazinedione, most preferably, diclazuril, which is (2,6-dichloro-α-(4-chlorophenyl)-4-(4,5-dihydro-3,5-dioxo-1,2,4-triazin-2(3H)-yl)benzeneacetonitrile).

In a preferred embodiment of the invention, the afflicted equine, e.g., a horse, is given a dose, twice a day, once a day, or every other day of triazinedione, which is equivalent to about 5–15 mg per kg of equine with or without food. More preferably, an equine is given a daily dose of 10 mg per kg of equine without food for at least about one month, or until testing for the protozoa proves negative. Twice a day, preferably once a day, administration of the active ingredient (e.g., say every morning in the feed) for at least about 3 months, preferably about 90–180 days, is generally found sufficient to treat the infection. In some cases, however, the treatment regimen can last indefinitely, sometimes for the remaining life of the horse. For ease of administration, the therapeutic composition may be given orally (that is, by mouth).

It should be apparent that an object of the present invention is the treatment of equine protozoan myeloencephalitis or EPM, including the alleviation of the symptoms of EPM, by providing and/or administering an effective amount of one or more triazinediones of formula (I):

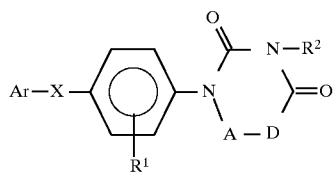

in which the group $R^1$ may be one or more of the same or different group selected from hydroxyl, thiol, carboxylic acid, carboxylic acid ester, sulfonic acid, sulfonic acid ester, alkoxy, thioalkoxy, linear or branched, saturated or unsaturated, substituted or unsubstituted alkyl or aryl group comprising 1–8 carbon atoms;

$R^2$ may be a linear or branched, saturated or unsaturated, substituted or unsubstituted alkyl or aryl group comprising 1–8 carbon atoms;

A—D represents the group

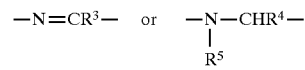

in which $R^3$ and $R^4$ may be a hydrogen, cyano, nitro, carboxylic acid, ester, or linear or branched, saturated or unsaturated alkylene chain or aryl group comprising 1–8 carbon atoms optionally substituted by hydroxyl, thiol, alkoxy, thioalkoxy, or halide groups and $R^5$ may be a linear or branched, saturated or unsaturated, substituted or unsubstituted alkylene chain or aryl group comprising 1–8 carbon atoms;

X may be an ether, sulfide, sulfoxide, sulfonyl, carbonyl, or a linear or branched, saturated or unsaturated alkylene chain comprising 1–8 carbon atoms optionally substituted by hydroxyl, thiol, alkoxy, thioalkoxy, halide, cyano, nitro, carboxylic acid, or ester groups; and Ar represents a substituted or unsubstituted aromatic group comprising 6–14 carbon atoms or a substituted or unsubstituted heteroaromatic group comprising 4–13 carbon atoms and one or more heteroatoms selected from nitrogen, oxygen, or sulfur, and the group Ar may be linked to the group X by a carbon atom or a heteroatom;

or a pharmaceutically acceptable salt thereof. Suitable salts thereof include, but not limited to, an acid addition salt, metal (e.g., alkali or alkaline earth) salt, or amine substitution salt. By the phrase "the group $R^1$ may be one or more of the same or different group" means that there can be one or more $R^1$ groups present on the phenyl ring, up to a maximum of four. Thus, the substituents $(R^1)_n$ can be present on the phenyl ring, in which n=1, 2, 3, or 4. In still other embodiments, the group $R^1$ may be absent and, hence, n may be 0. According to the present invention all stereoisomers of the various compounds of the formula (I) are contemplated, including racemic and optically active compositions thereof. A preferred triazinedione is diclazuril.

Convenient dosage formulations of the present invention are also contemplated, including solid and liquid forms and unit dosage forms containing therapeutically effective amounts ranging from about 1 to about 25 g, preferably about 2.5 to about 15 g, more preferably about 5 to about 10 g triazinedione.

These and other objects of the invention will become apparent to those of ordinary skill in the art, especially after consideration of the following detailed description of the preferred embodiments.

DETAILED DESCRIPTION OF THE PREFERRED EMBODIMENTS

The instant invention involves, in a preferred embodiment, the administration of an oral composition, containing triazinedione, such as diclazuril. The oral composition of the invention, such as a suspension or a tablet, overcomes the shortcomings of currently available treatments of EPM. It provides a more effective drug for horses and other equines infected with an organism of the genus Sarcocystis, especially *Sarcocystis neurona*, and especially those animals that are infected with a strain that proves resistant to available treatment. As previously mentioned, triazinedione may be given in a preferred dose of about 5 mg/kg equine to about 15 mg/kg equine, preferably about 7 mg/kg equine to about 12 mg/kg equine, more preferably, once daily at a dosage of about 10 mg/kg of equine.

It has been found that about a 5 g unit dose of an oral tablet (such as that described, infra) administered once or twice (preferably once) daily in their feed will provide adequate dosing for the treatment of EPM. Generally, the treatment period may be as short as about a month, to at least about 3 months, to as long as about six months. Because EPM is a protozoan infection of the central nervous system, the appropriate drug, formulation, or composition presumably must penetrate to the CNS where it can be available to counteract the protozoan infection. The substantial elimination of the cerebrospinal fluid titers for the protozoan marker can be used as a sign of successful treatment.

In a specific embodiment of the invention, the composition comprises about 2.8–6.8 g triazinedione, preferably about 3.2–5.5 g of triazinedione, per tablet. The liquid or solid composition may be prepared in unit dosage form depending upon the size of the equine. Such unit dosage forms may comprise about 1.5 to about 15 g of, preferably about 2 to about 10 g of, most preferably about 2.5 to about 5 g of each of one or more triazinediones. A preferred tablet comprises about 1, 2, 3, 5, 10, 15, 20 or more grams of diclazuril.

The present invention has been found to inhibit successfully the growth of the organism *Sarcocystis neurona* in equines, such as mules, donkeys, ponies and horses or domestic pets, such as dogs and cats, or zoo animals, such as monkeys. It is observed that the preferred triazinedione, diclazuril, can result in at least about a 50–70% rate of efficacy, perhaps at least about 80%, more perhaps at least 90%, or even more perhaps close to at least about 95% or 100% efficacy.

In line with the foregoing, it is within the contemplation of the present invention to employ compositions utilizing one or more triazinediones or their derivatives in treating EPM. The triazinediones of the present invention comprise a compound having the formula (I):

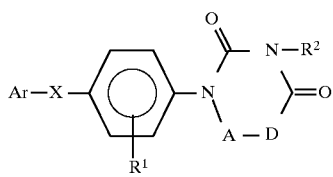

in which the group $R^1$ may be one or more of the same or different group selected from hydroxyl, thiol, carboxylic acid, carboxylic acid ester, sulfonic acid, sulfonic acid ester, alkoxy, thioalkoxy, linear or branched, saturated or unsaturated, substituted or unsubstituted alkyl or aryl group comprising 1–8 carbon atoms;

$R^2$ may be a linear or branched, saturated or unsaturated, substituted or unsubstituted alkyl or aryl group comprising 1–8 carbon atoms;

A—D represents the group

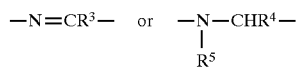

in which $R^3$ and $R^4$ may be a hydrogen, cyano, nitro, carboxylic acid, ester, or linear or branched, saturated or unsaturated alkylene chain or aryl group comprising 1–8 carbon atoms optionally substituted by hydroxyl, thiol, alkoxy, thioalkoxy, or halide groups and $R^5$ may be a linear or branched, saturated or unsaturated, substituted or unsubstituted alkylene chain or aryl group comprising 1–8 carbon atoms;

X may be an ether, sulfide, sulfoxide, sulfonyl, carbonyl, or a linear or branched, saturated or unsaturated alkylene chain comprising 1–8 carbon atoms optionally substituted by hydroxyl, thiol, alkoxy, thioalkoxy, halide, cyano, nitro, carboxylic acid, or ester groups; and Ar represents a substituted or unsubstituted aromatic group comprising 6–14 carbon atoms or a substituted or unsubstituted heteroaromatic group comprising 4–13 carbon atoms and one or more heteroatoms selected from nitrogen, oxygen, or sulfur, and the group Ar may be linked to the group X by a carbon atom or a heteroatom;

or a pharmaceutically acceptable salt thereof.

More preferably, the triazinedione is a compound of the formula (II):

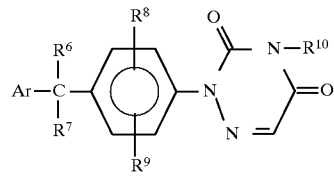

in which $R^6$ may be a hydroxy, cyano, or halide group and $R^7$ may be a hydrogen, $C_{1-6}$ alkyl, cyclo $C_{3-6}$ alkyl, phenyl, or phenyl substituted with up to three substituents each independently selected from halide, trifluoromethyl, $C_{1-6}$ alkyl, $C_{1-6}$ alkyloxy, $C_{1-6}$ alkylthio and $C_{1-6}$ alkylsulfonyloxy; $R^8$ and $R^9$ may each independently be hydrogen, halide, trifluoromethyl or $C_{1-6}$ alkyl; $R^{10}$ may be hydrogen or $C_{1-6}$ alkyl; and Ar may be a phenyl or phenyl substituted with up to three substituents each independently selected from halide, trifluoromethyl, $C_{1-6}$ alkyl, $C_{1-6}$ alkyloxy, $C_{1-6}$ alkylthio and $C_{1-6}$ alkylsulfonyloxy, or a pharmaceutically acceptable salt thereof.

Most preferably, the present invention employs compositions utilizing one or more triazinediones or their derivatives in treating EPM selected from the group consisting of: 2,6-dichloro-α-(4-chlorophenyl)-4-(4,5-dihydro-3,5-dioxo-1,2,4-triazin-2(3H)-yl)benzeneacetonitrile; 2-chloro-α-(4-chlorophenyl)-4-(4,5-dihydro-3,5-dioxo-1,2,4-triazin-2(3H)-yl)benzeneacetonitrile; 2-[4-[(6-chloro)2'-benzoxazolylsulphonyl]-3,5-dichlorophenyl]1,2,4-triazine-3,5(2H,4H)dione; 2-[4-[(4'-chloro)-2'-thiazolyloxy]phenyl]-3-N-methyl-3,5-(2H,4H)-dioxo-1,2,4-triazine; 2-[4-(4'-trifluoromethoxyphenyl-cyanomethyl)-3,5-dichlorophenoxy]-1,2,4-triazine-3,5-(2,4)dione; 2 [3,5-dichloro-4-(4-methylsulfonyl-phenoxy)-phenyl]-1-methylhexahydro-1,2,4-triazine-3,5-dione; or 1-[3,5-dichloro-4-pyridinyloxyphenyl]1,2,4-triazine-3,5-(2H,4H)-dione, or a pharmaceutically acceptable salt thereof.

The present compositions may be administered by routes well known to those skilled in the veterinary and formulation sciences. Therefore, although the triazinedione, for example, is conveniently administered orally, depending on the circumstances, the pharmaceutical composition may be administered parenterally, topically, intramucosally (e.g., intravaginally or rectally), or by other routes known to those skilled in this art.

Compositions suitable for oral administration, in addition to suspensions, include tablets, capsules, gels, pastes, boluses, or preparations in the form of powders, granules, or pellets. Preferred orally administered compositions include suspensions and tablets.

Alternatively, the composition may be administered parenterally by sub-cutaneous, intramuscular, intraperitoneal, or intravenous injection, or by implantation. The composition can be given as an intramammary injection whereby a suspension or solution is introduced into the udder.

Pharmaceutically acceptable carriers present in the compositions of the present invention are materials recommended for the purpose of administering the medicament. These may be liquid, solid, or gaseous materials, which are otherwise inert or medically acceptable and are compatible with the active ingredients. The same applies for any added excipients.

For oral administration, fine powders or granules can be selected. These compositions may optionally contain diluting agents, for example, calcium carbonate, calcium phosphate, mineral carriers, etc., dispersing and/or surface active agents, for example, polysorbates, and may be presented in a drench, in water or in a syrup, in a bolus, paste, or in capsules or sachets in the dry state or in a non-aqueous suspension, or in a suspension in water or syrup. Where desirable or necessary, preserving, suspending, thickening, or emulsifying agents can be included. If intended for oral use, a bolus will be provided with retention means to inhibit regurgitation. For example, it may be weighed with a heavy density material such as iron or tungsten or the like or may be retained by its shape, for example, by wings which spring after administration. Boluses may contain disintegrating agents such as maize starch or calcium or sodium methylcelluloses, hydroxypropylmethylcellulose, guar based vegetable gums, sodium alginates or sodium starch glycolates; granulating or binding agents, such as starch in the form of mucilage, starch derivatives, such as methylcellulose, calcium stearate, talc, gelatin or polyvinylpyrrolidone; and/or lubricating agents, such as magnesium stearate or stearic acid.

Other compounds which may be included are for example, medically inert ingredients, e.g. solid and liquid diluents, such as starch or calcium phosphate for tablets, boluses or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; dedusting agents such as liquid paraffin, fixed oils and surfactants and other therapeutically acceptable accessory ingredients, such as humectants, preservatives, buffers, and anti-oxidants, which are useful as carriers in such formulations. When desired, other medicaments and/or nutrients, such as vitamins or the like, unless contraindicated, may also be included.

Sweeteners may also be included such as dextrose, sucrose, nutrasweet, saccharine, sodium saccharin, fructose, lactose sorbitol, mannitol, glycerol, xylitol as well as hardeners such as, lactose.

It is also to be understood that while the preferred formulation is administered once a day, it may be given two or more times a day, depending on the circumstances. The triazinedione maybe given to the subject in its feed, or preferably, the triazinedione is given to the subject on an empty stomach. Also, a dosage of 5 mg per kg of afflicted equine may be advantageous.

The following discussion is provided to further describe the present invention. Indeed, it should be apparent that the present invention contemplates a method of treating equine protozoal myeloencephalitis (EPM) comprising administering to an equine suspected of suffering from EPM a therapeutically effective amount of one or more triazinediones. In particular, the one or more triazinediones are administered orally, preferably, daily. By the phrase "therapeutically effective amount" is meant that the amount administered is effective to inhibit the in vivo or in vitro growth of an organism belonging to the family Sarcocystidae, in particular, *Sarcocystis neurona*.

In a specific embodiment of the invention, the formulation used for treatment includes an effective amount of folic acid, which is administered over a dosage range (for a 1000-pound horse) of about 10 to about 75 mg, preferably about 30 to about 60, more preferably about 40 mg.

The triazinedione, e.g., diclazuril is administered in either a liquid or a solid form, preferably in the form of a solid tablet. Specifically, the present invention is directed to a veterinary composition in unit dosage form for the treatment of equine protozoan myeloencephalitis (EPM) comprising about 2 to about 20 g of a triazinedione, about 1 to about 10 g of lactose, about 0.5 to about 5 g of a cellulosic ingredient, about 50 to about 500 mg of a fatty acid salt and about 10 to about 1000 mg of an artificial sweetener. In one embodiment, the composition is in the form of an oral suspension comprising about 300 to about 700, preferably, 500 g diclazuril per liter of composition. In certain cases, it might be advantageous not to include substantial amounts of natural sugars. More preferably, the unit dosage comprises about 2.5 to about 15 g diclazuril, most preferably, about 5 g diclazuril.

The present invention also relates to a method of treating an animal suffering from a condition brought about by an organism belonging to the family Sarcocystidae, comprising administering to the animal a therapeutically effective amount of one or more triazinediones. The treatment methods contemplated can be applied to a large number of warm-blooded animals, including equines, canines, felines, or primates, especially a horse suffering from equine protozoal myeloencephalitis (EPM).

A further appreciation of the invention may be gleaned from the following specific examples. These specific examples are provided for illustration only and are not to be regarded as restricting the invention in any way.

EXAMPLES

Triazinediones useful in the present invention may be prepared according to known methods. In particular, the interested reader is referred to the disclosures of U.S. Pat. Nos. 4,912,106 and 4,631,278, which are incorporated in their entirety by reference herein.

For the preferred traizinedione, diclazuril, the following synthetic method is described.

Synthesis

To a stirred mixture of 45.3 parts of 1,2,3-trichloro-5-nitrobenzene, 300 parts of a 50% aqueous sodium hydroxide solution, 5 parts of N,N,N-triethylbenzenemethanaminium chloride and 360 parts of tetrahydrofuran is added dropwise, during a 5 minutes period, a solution of 33.3 parts of 4-chlorobenzene-acetonitrile in 90 parts of tetrahydrofuran. Upon completion, stirring is continued for 4 hours at 50 degrees C. The reaction mixture is poured into 1500 parts of crushed ice and acidified with concentrate hydrochloric acid. The product is extracted with trichloromethane. The extract is dried, filtered and evaporated. The residue is stirred in 2,2'-oxybispropane. The product is filtered off and dried, yielding 63.8 parts (93.3%) of 2,6-dichloro-α-(4-chlorophenyl)-4-nitrobenzeneacetonitrile (intermediate 1).

A mixture of 31.1 parts of 2,6-dichloro-α-(4-chlorophenyl)-4-nitrobenzeneacetonitrile (intermediate 1), 2 parts of a solution of 4% thiophene in methanol and 480 parts of methanol is hydrogenated in the Parr apparatus at 50 degrees C with 3 parts of 5% platinum-on-charcoal catalyst. After the calculated amount of hydrogen is taken up, the catalyst is filtered off, washed with tetrahydrofuran and the filtrate is evaporated in vacuo. The residue is crystallized from 160 parts of 2-propanol. The product is filtered off, washed with 2,2'-oxybispropane and dried, yielding 4-amino-2,6-dichloro-α-(4-chlorophenyl) benzeneacetonitrile. (intermediate 2).

To a stirred and cooled (5–10 degrees C) mixture of 15.2 parts of 4-amino-2,6-dichloro-α-(4-chlorophenyl)-benzeneacetonitrile (intermediate 2), 14.4 parts of concentrate hydrochloric acid and 125 parts of acetic acid is added dropwise, during a 30 minutes period, a solution of 3.5 parts of sodium nitrite in 15 parts of water at about 10 degrees C. Upon completion, the whole is stirred for 30 minutes and then 10 parts of sodium acetate and 7.8 parts of ethyl(2-cyanoacetyl)carbamate are added, during a period of 2 hours, at room temperature. The reaction mixture is poured into 500 parts of water. The product is filtered off, washed with water and dissolved in dichloromethane. The organic layer is dried, filtered and evaporated. The residue is purified by column chromatography over silica gel using a mixture of trichloromethane and methanol (95:5 by volume) as eluent. The pure fractions are collected and the eluent is evaporated in vacuo. The residue is stirred in 2-propanol. The product is filtered off, washed with 2,2'-oxybispropane and dried, yielding ethyl[2-[[3,5-dichloro-4-[(4-chlorophenyl)cyanomethyl]phenyl]hydrazono]-2-cyanoacetyl]carbamate (intermediate 3).

A mixture of 7.8 parts of ethyl[2-[[3,5-dichloro-4-[(4-chlorophenyl)cyanomethyl]phenyl]hydrazono]-2-cyanoacetyl]carbamate (intermediate 3), 1.98 parts of anhydrous potassium acetate and 120 parts of acetic acid is stirred and heated under reflux for 3 hours. The reaction mixture is concentrated to a volume of 30 parts. Water is added until the product is precipitated. It is sucked off, washed with water and dissolved in trichloromethane. The remaining water is separated and the organic phase is dried, filtered and evaporated, yielding 2-[3,5-dichloro-4-[(4-chlorophenyl) cyanomethyl]phenyl]-2,3,4,5-tetrahydro-3,5-dioxo-1,2,4-triazine-6-carbonitrile (intermediate 4).

A mixture of 6.86 parts of 2-[3,5-dichloro-4-[(4-chlorophenyl)cyanomethyl]phenyl]-2,3,4,5-tetrahydro-3,5-dioxo-1,2,4-triazine-6-carbonitrile (intermediate 4), 30 parts of concentrate hydrochloric acid and 150 parts of acetic acid is stirred and heated under reflux for 24 hours. The reaction mixture is evaporated and the residue is dissolved in trichloromethane. The latter is dried, filtered and evaporated, yielding 2-[3,5-dichloro-4-[(4-chlorophenyl)cyanomethyl] phenyl]-2,3,4,5-tetrahydro-3,5-dioxo-1,2,4-triazine-6)-carboxylic acid (intermediate 5).

A mixture of 11.1 parts of 2-[3,5-dichloro-4-[(4-chlorophenyl)cyanomethyl]phenyl]-2,3,4,5-tetrahydro-3,5-dioxo-1,2,4-triazine-6-carboxylic acid (intermediate 5) and 15 parts of 2-mercaptoacetic acid is stirred and heated for 2 hours at 180 degrees C. The reaction mixture is cooled, water is added and the whole is treated with sodium hydrogen carbonate. The product is extracted with trichloromethane. The organic layer is dried, filtered and evaporated. The residue is purified by column chromatography over silica gel using a mixture of trichloromethane and methanol (95:5 by volume) as eluent. The pure fractions are collected and the eluent is evaporated in vacuo. The residue is stirred in 2,2'-oxybispropane. The product is filtered off and dried, yielding 2,6-dichloro-α-(4-chlorophenyl)-4-(4,5-dihydro-3,5-dioxo-1,2,4-triazin-2(3H)-yl) benzeneacetonitrile.

Other triazinediones can be prepared similarly, following the procedure described above, with appropriate modifications. These compounds include, but are not limited to, 2-chloro-α-(4-chlorophenyl)-4-(4,5-dihydro-3,5-dioxo-1,2,4-triazin-2(3H)-yl)benzeneacetonitrile (Compound 1); 2-[4-[(6-chloro) 2'-benzoxazolylsulphonyl]-3,5-dichlorophenyl] 1,2,4-triazine-3,5(2H,4H)dione (Compound 2); 2-[4-[(4'-chloro)-2'-thiazolyloxy]phenyl]-3-N-methyl-3,5-(2H,4H)-dioxo-1,2,4-triazine (Compound 3); 2-[4-(4'-trifluoromethoxyphenyl-cyanomethyl)-3,5-dichlorophenoxy]-1,2,4-triazine-3,5-(2,4)dione (Compound 4); 2 [3,5-dichloro-4-(4-methylsulfonyl-phenoxy)-phenyl]-1-methylhexahydro-1,2,4-triazine-3,5-dione (Compound 5); 1-[3,5-dichloro-4-pyridinyloxyphenyl]1,2,4-triazine-3,5-(2H,4H)-dione (Compound 6), or pharmaceutically acceptable salts thereof.

Veterinary compositions effective for the general treatment of EPM are provided, below, in the form of an oral tablet. As mentioned above, a useful dosage, e.g., for a 1,000 pound horse infected with *Sarcocystis neurona* (as evidenced by the presence of the protozoan in a sample from the subject's cerebrospinal fluid) is about one tablet containing about 4.5 g of active ingredient, once a day, with or without food (preferably on an empty stomach).

| Formulation A | |
|---|---|
| Component | Weight |
| 1. Diclazuril (or Compound 1) | 2.5 g |
| 2. Lactose | 1.25 g |
| 3. Methylcellulose | 0.5 g |
| 4. Magnesium Stearate | 85 mg |
| 5. Nutrasweet | 200 mg |

Preferably, the composition does not contain substantial amounts of natural sugars. Most preferably, the composition is substantially free of natural sugars as some of the triazinedione may be sensitive to the presence of naturally occurring sugars. Optionally, folic acid may also be administered to the subject, at a separate time. Typically, the subject may receive about 40 mg of folic acid per 500 to 1000 pound equine.

The triazinedione may also be administered substantially concurrently, or at another time of the day, with a composition comprising pyrimethamine and a sulfonanamide, wherein the relative weight ratio of the pyrimethamine to the sulfonamide is about 1:10 to about 1:30 and the dosage comprises about 0.5 to about 2 mg/kg of pyrimethamine and about 15 to about 30 mg/kg of sulfonamide. Sulfonamides can be selected from the group consisting of sulfachlorpyridazine, sulfadimethoxine, sulfamerazine, sulfamethazine, sulfamethoxypyridazine, sulfaphenazole, sulfapyrazine and sulfisomidine. the sulfonamide is sulfadiazine. Preferably the sulfonamide is sulfadiazine.

A stepwise procedure for the preparation of the oral tablets is provided below:

(i) the powders of the formulation are mixed by geometric dilution until a uniform mixture is achieved;

(ii) a sample of the uniform mixture is then placed in a tablet machine where the sample is pressed into a tablet form and the machine is calibrated such that the tablet resists breaking under finger pressure or is hard enough to resist breaking when dropped from a height of about five feet; and (iii) after calibrating in step (ii), continuously add the uniform mixture to the tablet press and press the mixture into tablets forms.

As further illustrations of the composition of the invention, the following descriptions of suitable alternative formulations are provided.

| Component | Weight |
|---|---|
| Formulation B | |
| 1. Diclazuril (or Compound 2) | 3.0 g |
| 2. Lactose | 1.5 g |
| 3. Methylcellulose | 0.6 g |
| 4. Magnesium Stearate | 100 mg |
| 5. Nutrasweet | 200 mg |
| Formulation C | |
| 1. Diclazuril (or Compound 3) | 5.0 g |
| 2. Lactose | 2.5 g |
| 3. Methylcellulose | 1.0 g |
| 4. Magnesium Stearate | 175 mg |
| 5. Nutrasweet | 35 mg |
| Formulation D | |
| 1. Diclazuril (or Compound 4) | 10.0 g |
| 2. Lactose | 5.0 g |
| 3. Methylcellulose | 2.0 g |
| 4. Magnesium Stearate | 333 mg |
| 5. Nutrasweet | 667 mg |
| Formulation E | |
| 1. Diclazuril (or Compound 5) | 15.0 g |
| 2. Lactose | 7.5 g |
| 3. Methylcellulose | 3.0 g |
| 4. Magnesium Stearate | 500 mg |
| 5. Saccharin | 1.0 g |
| Formulation F | |
| 1. Diclazuril (or Compound 6) | 5.0 g |
| 2. Lactose | 2.5 g |
| 3. Methylcellulose | 1.0 g |
| 4. Magnesium Stearate | 175 mg |
| 5. Saccharin | 35 mg |

Only the preferred embodiment of the invention and but a few examples of its versatility are shown and described in the present disclosure. It is to be understood that the invention is capable of use in various other combinations and environments and is capable of changes and modifications within the scope of the inventive concept as expressed herein.

What is claimed is:

1. A method of treating equine protozoal myeloencephalitis (EPM) comprising administering to an equine suspected of suffering from EPM a therapeutically effective amount of one or more triazinediones.

2. The method of claim 1 in which the one or more triazinediones are administered orally.

3. The method of claim 1 in which the one or more triazinediones are administered daily.

4. The method of claim 1 the therapeutically effective amount is effective to inhibit the growth of an organism belonging to the family Sarcocystidae.

5. The method of claim 4 in which the organism is *Sarcocystis neurona*.

6. The method of claim 1 in which the one or more triazinediones comprise a compound having the formula (I):

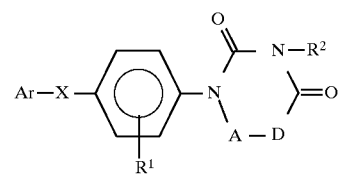

in which the group $R^1$ may be one or more of the same or different group selected from hydroxyl, thiol, carboxylic acid, carboxylic acid ester, sulfonic acid, sulfonic acid ester, alkoxy, thioalkoxy, linear or branched, saturated or unsaturated, substituted or unsubstituted alkyl or aryl group comprising 1–8 carbon atoms;

$R^2$ may be a linear or branched, saturated or unsaturated, substituted or unsubstituted alkyl or aryl group comprising 1–8 carbon atoms;

A—D represents the group

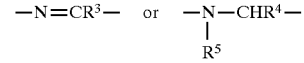

in which $R^3$ and $R^4$ may be a hydrogen, cyano, nitro, carboxylic acid, ester, or linear or branched, saturated or unsaturated alkylene chain or aryl group comprising 1–8 carbon atoms optionally substituted by hydroxyl, thiol, alkoxy, thioalkoxy, or halide groups and $R^5$ may be a linear or branched, saturated or unsaturated, substituted or unsubstituted alkylene chain or aryl group comprising 1–8 carbon atoms;

X may be an ether, sulfide, sulfoxide, sulfonyl, carbonyl, or a linear or branched, saturated or unsaturated alkylene chain comprising 1–8 carbon atoms optionally substituted by hydroxyl, thiol, alkoxy, thioalkoxy, halide, cyano, nitro, carboxylic acid, or ester groups; and Ar represents a substituted or unsubstituted aromatic group comprising 6–14 carbon atoms or a substituted or unsubstituted heteroaromatic group comprising 4–13 carbon atoms and one or more heteroatoms selected from nitrogen, oxygen, or sulfur, and the group Ar may be linked to the group X by a carbon atom or a heteroatom;

or a pharmaceutically acceptable salt thereof.

7. The method of claim 1 in which the one or more triazinediones comprise a compound having the formula (II):

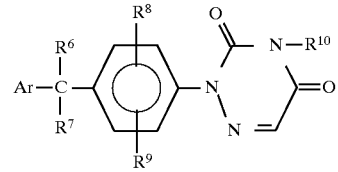

in which $R^6$ may be a hydroxy, cyano, or halide group and $R^7$ may be a hydrogen, $C_{1-6}$ alkyl, cyclo $C_{3-6}$ alkyl, phenyl, or phenyl substituted with up to three substituents each independently selected from halide, trifluoromethyl, $C_{1-6}$ alkyl, $C_{1-6}$ alkyloxy, $C_{1-6}$ alkylthio and $C_{1-6}$ alkylsulfonyloxy; $R^8$ and $R^9$ may each independently be hydrogen, halide, trifluoromethyl or $C_{1-6}$ alkyl; $R^{10}$ may be hydrogen or $C_{1-6}$ alkyl; and Ar may be a phenyl or phenyl substituted with up to three substituents each independently selected from halide, trifluoromethyl, $C_{1-6}$ alkyl, $C_{1-6}$ alkyloxy, $C_{1-6}$ alkylthio and $C_{1-6}$ alkylsulfonyloxy, or a pharmaceutically acceptable salt thereof.

8. The method of claim 7 in which the one or more triazinediones comprise a compound selected from the group consisting of 2-chloro-α-(4-chlorophenyl)-4-(4,5-dihydro-3,5-dioxo-1,2,4-triazin-2(3H)-yl)benzeneacetonitrile; 2-[4-[(6-chloro)2'-benzoxazolylsulphonyl]-3,5-dichlorophenyl],1,2,4-triazine-3,5(2H,4H)dione; 2-[4-[(4'-chloro)-2'-thiazolyloxy]phenyl]-3-N-methyl-3,5-(2H,4H)-dioxo-1,2,4-triazine; 2-[4-(4'-trifluoromethoxyphenyl-cyanomethyl)-3,5-dichlorophenoxy]-1,2,4-triazine-3,5-(2,4)dione; 2 [3,5-dichloro-4-(4-methylsulfonyl-phenoxy)-phenyl]-1-methylhexahydro-1,2,4-triazine-3,5-dione; 1-[3,5-dichloro-4-pyridinyloxyphenyl]1,2,4-triazine-3,5-(2H,4H)-dione, or a pharmaceutically acceptable salt thereof.

9. The method of claim 7 in which the one or more triazinediones comprise the compound diclazuril, which is 2,6-dichloro-α-(4-chlorophenyl)-4-(4,5-dihydro-3,5-dioxo-1,2,4-triazin-2(3H)-yl)benzeneacetonitrile or a pharmaceutically acceptable salt thereof.

10. The method of claim 9 in which the diclazuril is administered daily at a dosage of about 5 to about 15 mg/kg of equine.

11. The method of claim 9 in which the diclazuril is administered once daily at a dosage of about 10 mg/kg of equine.

12. The method of claim 11 in which the diclazuril is administered once daily for a period of at least about one month.

13. The method of claim 11 in which the diclazuril is administered once daily for a period of at least about three months.

14. The method of claim 1 which further comprises administering an effective amount of folic acid.

15. The method of claim 14 in which the folic acid is administered daily at a dosage of about 40 mg per 1000-pound equine.

16. The method of claim 9 in which the diclazuril is administered in either a liquid or a solid form.

17. The method of claim 16 in which the diclazuril is administered in the form of a solid tablet.

18. A veterinary composition in unit dosage form for the treatment of equine protozoan myeloencephalitis (EPM) comprising about 2 to about 20 g of a triazinedione, about 1 to about 10 g of lactose, about 0.5 to about 5 g of a cellulosic ingredient, about 50 to about 500 mg of a fatty acid salt and about 10 to about 1000 mg of an artificial sweetener.

19. The composition of claim 18 in which the triazinedione comprises diclazuril.

20. The composition of claim 18 which is an oral suspension.

21. The composition of claim 20 in which the diclazuril is present in an oral composition comprising about 500 g diclazuril per liter of composition.

22. The composition of claim 21 which does not include substantial amounts of natural sugars.

23. The composition of claim 20 in which the unit dosage comprises about 2.5 to about 15 g diclazuril.

24. The composition of claim 23 in which the unit dosage comprises about 5 g diclazuril.

25. A method of treating an animal suffering from a condition brought about by an organism belonging to the family Sarcocystidae, comprising administering to the animal a therapeutically effective amount of one or more triazinediones.

26. The method of claim 25 in which the animal is an equine, canine, feline, or primate.

27. The method of claim 25 in which the animal is a horse suffering from equine protozoal myeloencephalitis (EPM).

* * * * *